United States Patent [19]
Standley

[11] Patent Number: 5,830,235
[45] Date of Patent: Nov. 3, 1998

[54] PACIFIER SYSTEM AND METHOD OF THERAPEUTICALLY TREATING INFANT SUCKING RESPONSE

[75] Inventor: Jayne M. Standley, Tallahassee, Fla.

[73] Assignee: Florida State University, Tallahassee, Fla.

[21] Appl. No.: 972,191

[22] Filed: Nov. 18, 1997

[51] Int. Cl.⁶ ..................................... A61J 17/00
[52] U.S. Cl. .................. 606/234; 606/234; 606/235; 606/236; 40/455
[58] Field of Search .................. 606/234, 235, 606/236; 40/455

[56] References Cited

U.S. PATENT DOCUMENTS

| | | |
|---|---|---|
| D. 371,201 | 6/1996 | Gipson et al. . |
| 4,554,919 | 11/1985 | Hubert . |
| 4,640,034 | 2/1987 | Zisholtz ..................................... 40/455 |
| 4,856,519 | 8/1989 | Teves . |
| 4,969,867 | 11/1990 | Cohen . |
| 5,033,864 | 7/1991 | Lasecki et al. ........................ 606/234 |
| 5,292,335 | 3/1994 | Shin . |

OTHER PUBLICATIONS

A.J. DeCasper & W.P. Fifer, "Of Human Bonding: Newborns Prefer Their Mothers'Voices", 1980, pp. 1174–1176.
A.J. DeCasper & A.D. Sigafoos, "The Intrauterine Heartbeat: A Potent Reinforcer for Newborns", 1983, pp. 19–25.
A.J. DeCasper & P.A. Prescott, "Human Newborns'Perception of Male Voices: Preference, Discrimination, and Reinforcing Value", 1984, pp. 481–491.
M.J. Spence & A.J. DeCasper, "Prenatal Experience with Low–Frequency Maternal–Voice Sounds Influence Perception of Maternal Voice Samples", 1987, pp. 133–142.

*Primary Examiner*—Michael Powell Buiz
*Assistant Examiner*—Vy Q. Bui
*Attorney, Agent, or Firm*—A. Jose Cortina; Kilpatrick Stockton LLP

[57] ABSTRACT

A pacifier system and method of therapeutically treating premature infants to reinforce non-nutritive sucking is disclosed. A pacifier is connected to a pressure transducer. The pressure tranducer serves to detect sucking intensity and time of sucking. The pacifier system activates a sound source, such as a music source, upon sucking of a minimum intensity being detected for a minimum period of time.

20 Claims, 4 Drawing Sheets

PACIFIER SYSTEM AND METHOD OF THERAPEUTICALLY TREATING INFANT SUCKING RESPONSE

BACKGROUND OF THE INVENTION

This invention relates to pacifier system for reinforcing non-nutritive sucking rates of premature infants, for assisting normal infants to learn music and language and for use with cerebral palsied infants, paralyzed infants or otherwise handicapped infants to facilitate activation of an auditory stimulus device such as a tape player, C.D. player or other like device.

Currently there exist a number of pacifier devices, which include such things as melody generators, and which serve to play music when an infant sucks on a pacifier as an additional means of tranquilizing the infant, for example, into sleep.

One such prior art device is a sound generating pacifier for use by an infant which includes a pacifier body having a first end and a second end with an air passageway extending therebetween. The pacifier body includes a pacifier guide for preventing an infant from choking or swallowing the pacifier when in use. A nipple is disposed at the first end of the pacifier and includes an apperature formed therein to enable in use air communication between the mouth of the infant and the air passageway of the pacifier body. A sound generator serves to directly generate sound upon air flowing through the sound generator, and is positioned at the second end of the pacifier body. The sound generator is in air communication with the air passageway of the pacifier body, and a one way valve inhibits the flow of the air through the ai pacifier body and into the mouth of the infant when the infant sucks on the nipple, and enables the expired air from the mouth of the infant to flow through the apperature of the nipple. The air exits the sound generator to thereby cause it to generate sound upon the sucking action of an infant.

Another such device is a musical pacifier which includes a mouth piece having a single portion and a single casing secured to the mouth piece for housing an electronic programmed circuit capable of generating signals to produce a musical tune. A sound generator is located with the circuit to audibly reproduce the signals. A switch is provided which serves to actuate the electronic programmed circuit. When the switch contact is closed, a power cell battery is connected to the electronic program circuit to activate the circuit to produce signals which are generated by a speaker element in the pacifier. Thus, the electronic programmed circuit is switched on and off by the infant compressing and decompressing the nipple which is the natural action that an infant performs when sucking on a nipple.

It is also possible in this type of device to provide a time delay shorting circuit which may be connected across the switch contact so that a single switch closure shorts the switch out automatically, and the electronic programmed circuit is inactivated for a predetermined period of time. For example, the predetermined period of time can be calculated to permit the programmed circuit to produce signals of a complete musical tune, and after the predetermined time delay, the shorting circuit deactivates itself. If the switch clement is again closed, the device will again active itself and cause the program circuit to generate a complete musical tune.

Yet still another prior art device is an infant pacifier having a diaphragm melody generator in which when the infant holds the pacifier in the mouth and sucks or mumbles, a diaphragm switch of the melody generator operates to turn the melody generator on in order to permit the generator to generate a melody. The melody generator includes a diaphragm switch for turning on/off the melody generator in accordance with the holding force, and an electronic circuit board serves to generate the melody in cooperation with the diaphragm switch when the infant holds the nipple part of the pacifier in the mouth and sucks or mumbles it to cause the nipple part to be compressed, thereby causing a pressure transfer of inner pressure of the pacifier from the nipple part to the diaphragm switch.

An alternative pacifier type device of the prior art includes an apparatus for promoting sleep in an individual made up of a blanket, mattress, pillow or similar article adapted to be placed against and/or around an individual. A plurality of compressional wave transducers are incorporated into the article and distributed over a relatively large surface area at a plurality of different locations for producing compressional waves at the locations. An electrical circuit serves to generate electrical signals energizing the transducers to produce sleep-promoting compressional waves at the plurality of different locations. The wave transducers may be sonic, supersonic or subsonic, such as the constrictive or expansive type. As one example, there may be used small speakers which produce audible sounds. In one embodiment, the signal generator generates an electric signal simulating the human heart beat. A sound sensor serves to sense the crying of the infant and is effective in response thereto, to actuate the signal generator. An attenuator can be provided for causing the sounds to fade out at a preselected rate after a period of time. While all of the prior art devices provide a pacifier function, they fail to combine the pacifier function with a system and method of therapeutically using the pacifier function to enhance the non-nutritive sucking rates of premature infants, teach language and music to normal infants, and/or provide a control system for handicapped infants such as cerebral palsied or paralyzed infants.

SUMMARY OF THE INVENTION

Thus, in accordance with one aspect of the invention, there is provided a pacifier system for modifying a response. The pacifier system includes a pacifier for being sucked thereon. A sensor serves to sense duration and intensity of sucking on the pacifier. A device for providing auditory stimulus is included in the system. Activating means such as a switch, serves to activate the device for providing auditory stimulus for a predetermined amount of time upon the sensor sensing sucking on the pacifier for a predetermined minimum amount of time, and of a minimum intensity. The response can be a sucking response and the system is used therapeutically to teach a particular type of response, for example, non-nutritive sucking by premature infants. Alternatively, the device, while used to achieve a type of sucking response, may merely be used to provide entertainment, although the providing of entertainment is tied to the response achieved.

In a more preferred aspect, the device for providing auditory stimulus is a source of played music. The sensor is preferably adapted for detecting a specified suck profile which when detected, causes the means for activating the auditory stimulus device to activate the stimulus device. Yet more preferably, the sensor is adapted to detect minimum intensity of sucking, minimum duration of sucking, maximum duration of sucking, minimum frequency of sucking and maximum frequency of sucking to determine the suck profile.

In another aspect of the invention, there is provided a method of modifying a sucking response. The method includes the steps of detecting the intensity of sucking and duration of sucking on a pacifier. Upon detection of a predetermined intensity of sucking for a predetermined amount of time, there is provided an auditory stimulus.

More preferably, the detecting step involves detecting the sucking of a premature infant on a pacifier, and includes detecting the sucking profile of the sucking, and only providing the auditory stimulus upon the sucking matching a predetermined sucking profile. Yet still more preferably, a predetermined sucking profile is determined by detecting the values of a minimum intensity of sucking, a minimum duration of sucking, a maximum duration of sucking, a minimum frequency of sucking, and a maximum frequency of sucking, whereby only sucking profiles falling within the noted values are used to provide the auditory stimulus.

BRIEF DESCRIPTION OF THE DRAWINGS

Having thus briefly described the invention, the same will become better understood from the following detailed discussion, taken in conjunction with the appended drawings wherein.

DETAILED DESCRIPTION OF THE INVENTION

Figure 1:
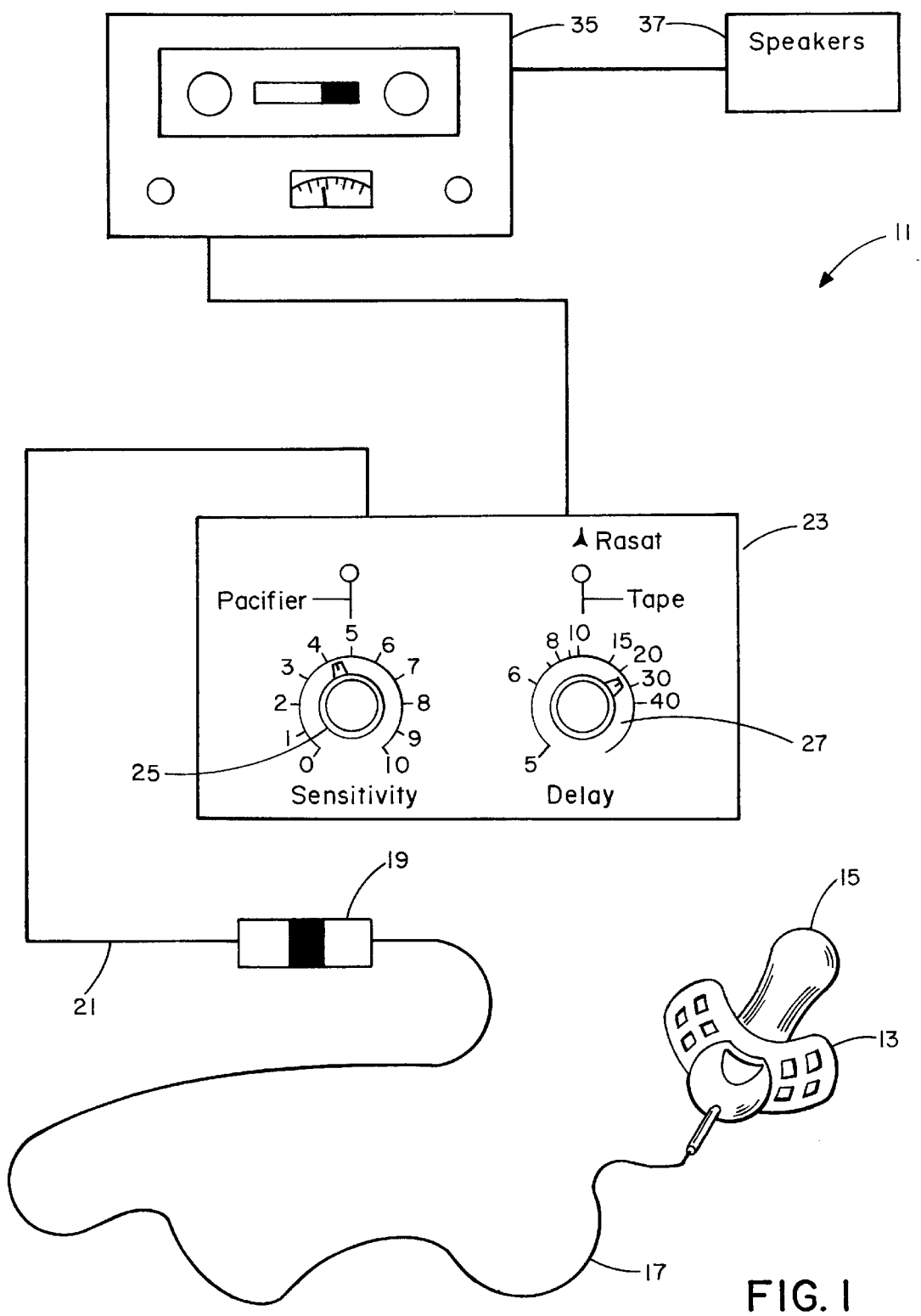
FIG. 1 is a schematic diagram of a first embodiment of the pacifier system in accordance with the invention.

FIG. 1 schematically illustrates a first embodiment of the pacifier system 11 in accordance with the invention. A pacifier 13 includes a nipple portion 15 connected through an air tube 17 through sensing means such as a pressure sensor 19. The pressure sensor 19 is in turn connected through an electrical line 21 to means for activating an auditory stimulus source. Specifically such means for activating can be a control box 23 of conventional construction which includes a sensitivity control dial 25 and delay control dial 27. The sensitivity control dial 25 is used to set the sensitivity of detection of pressure being exerted on a nipple 15 of the pacifier 13 and the delay dial 27 is used to set the time that sucking of predetermined minimum intensity, as set with the sensitivity control dial 25, must occur before a signal is sent for example, to an auditory source such as a tape recorder 35 to begin to play music and broadcast it through connected speaker(s) 37. With respect to the control box 23, this is of conventional construction, having an appropriate sensitivity circuit and time delay circuit built into the control box 23. The tape recorder 35 is also a conventional construction, such as one commercially available from Radio Shack and known as the CTR-62 cassette tape recorder. Similarly, the pressure transducer is a conventional transducer capable of detecting specified changes in air pressure in the air tube 17.

Thus, in operation, the pressure transducer 19 through the control box 23 serves to activate a tape recorder for a predetermined amount of time by sensing pressure changes in the pacifier 13 connected to the pressure sensor 19. In a preferred mode of operation, the delay dial 27 is set to a minimum of five seconds of delay to about two minutes and forty seconds maximum delay. The sensitivity dial 25 is set at a sufficiently low position to avoid having the tape player 35 play with just a slight pull on the pacifier nipple 15. The tape recorder 35 is set on play, but due to the connection to the control box 23, is only activated upon the nipple 15 being sucked on at a minimum intensity and for a predetermined minimum of time, at which time the control box 23 allows the tape player 35 to begin playing and to broadcast music through speaker(s) 37.

Figure 2:
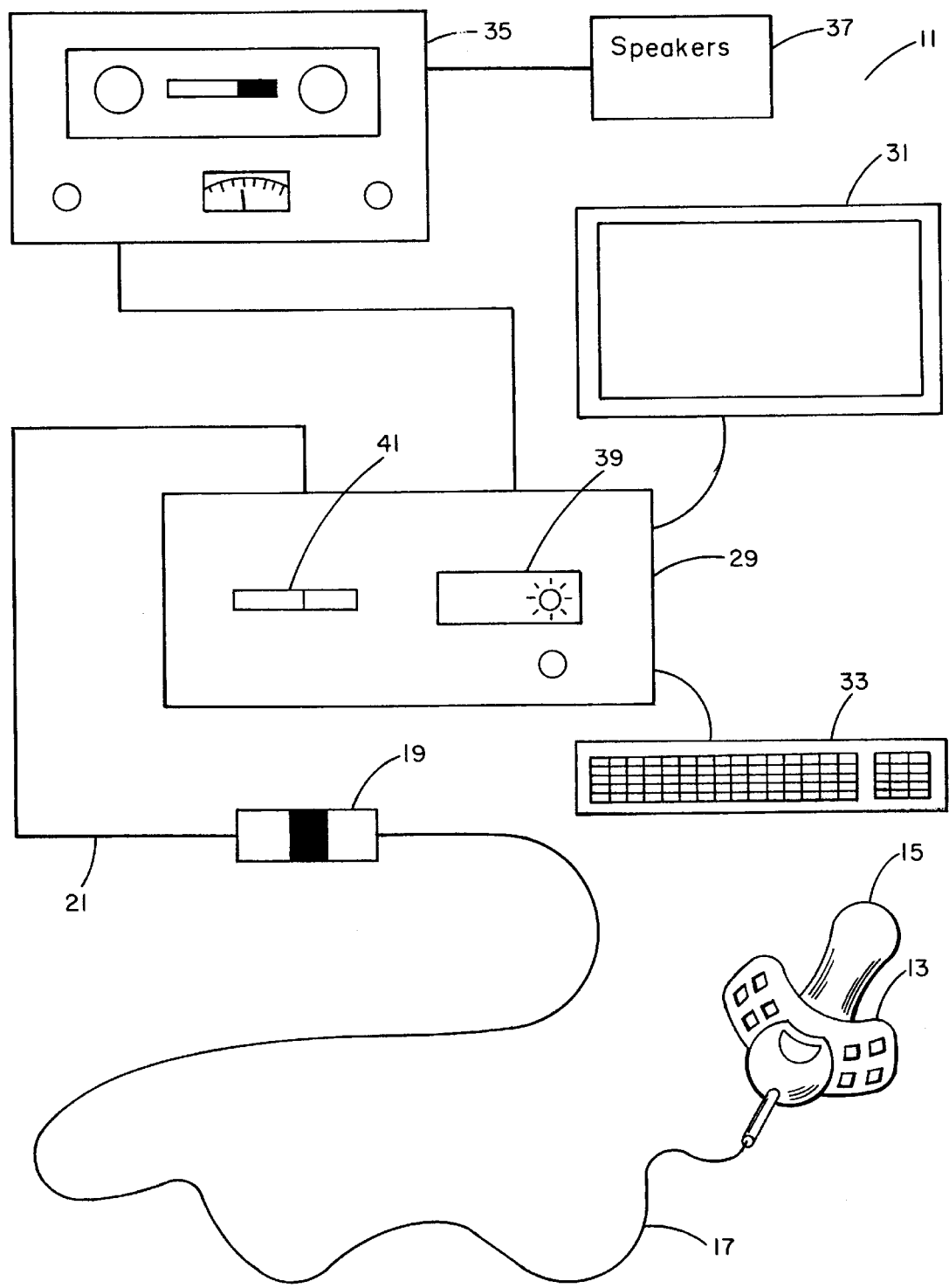
FIG. 2 is a schematic diagram of a second embodiment of the pacifier system in accordance with the invention.

An alternative embodiment to the pacifier system 11 in accordance with the invention is shown in FIG. 2 in which the means for activating the auditory stimulus device is a general purpose computer 29, such as a personal computer including a hard drive 39 and floppy disk drive 41. This type of device is used in place of the controller box 23. Software is programmed into the personal computer 29 and operated on through keyboard 33 with an appropriate display of the operation thereof being exhibited through display 31. Although use of the tape recorder 35 has been described, it will be readily apparent to those of ordinary skills in the art that the tape recorder 35 can be replaced with any conventional sound source such as a compact disk player or other similar type device.

The advantage of a computer 29 based system in accordance with that shown in FIG. 2 is that greater flexibility is provided by appropriate software which has been developed in a conventional manner. For example, not only can intensity of sucking be now measured, but five suck parameter thresholds can be detected to allow matching to a prototype sucking profile of normal, i.e., full term, infants as established by use of the device. Typical profiles will include detected minimum intensity, minimum duration, maximum duration, minimum frequency and maximum frequency of sucking. Thus, the player 35 will only play music when the sucking profile falls between the detected parameters, i.e., fall between the minimum and maximum duration limits and are repeated at a proper frequency across time. The infant suck profile can be collected by frequency modulated recording of the analog suction waveform which can be stored in the computer 29 and simultaneously displayed on monitor 31 to provide an immediate indication of the infants oral activity. As may be appreciated, the variables described can be adjusted as time progresses based on the infant's performance.

In an alternative intermediate development, it may not be necessary to employ a programed personal computer 29, and instead a tape recorder can be used to continuously collect the infant suck profile as a Frequency Modulated (FM) tape recording of the analog section waveform. The Frequency Modulated (FM) tone can then be broadcast by a separate speaker (not shown), i.e., not the speaker 37 used to play music. The broadcast can be monitored by a user such as a researcher, parent or staff to provide an immediate indication of the infant's oral activity.

The system 11 in accordance with the invention, particularly that of FIG. 1 is used to determine whether pacifier activated lullaby music reinforces non-nutritive sucking rates of premature infants deemed for feeders. Participants in a test conducted were twelve premature infants born at an average gestation age of 29.3 weeks and an average weight of 2 lbs. 4.8 oz. The average adjusted gestation age at the time of the test study was 35.5 weeks with weight averaging 3 lbs. 8.6 oz.

The pacifier system 11 of FIG. 1 was adapted so that a suck of predetermined strength and of sufficient time activated a tape recording and illuminated a signal light to provide a visual indication. Pressure sensitivity and length of music activation was controlled for each suck and for the purpose of this study was set at 15% pressure to activate ten seconds of music. The music was a selection of commercially recorded lullabies sung by a female vocalist.

The study was conducted across fourteen minutes with a silent condition for the first two minutes of baseline, then five minutes of music, followed by another two minute period of silence and another five minutes of music. Data were recorded across the fourteen minutes for each five second intervals during which an indicator light indicating sucking was activated for at least three seconds.

The results of the test demonstrated that music sucking rates were 2.43 times as great as silent sucking rates. The data indicated that infant learning and discrimination of music on/off conditions occurred, and showed music to be an effective reinforcer for non-nutritive sucking for the limited time period.

It is believed that the system and method in accordance with the invention is useful because in the third trimester, the human fetus is typically adding 250,000 neurons per minute in the developing brain. During fetal development and at birth, neural cells complete the link up with a specific neurological function. The newborn infant is therefore, self constructing with post birth experiences creating unique connections for each individual.

In the case of a premature birth, the premature infant loses the opportunity to continue neurological development in the safe, nurturing environment of the womb. Those with medical complications are subjected to painful and stressful procedures necessitated for survival which in turn result, based on existing correlations, with increased impairment in neurological development. However, the brain continues to develop throughout life and damaged neurological networks can often be overcome by nurturing and carefully structured learning.

Research with premature infants in intensive care units has primarily focused on medical procedures and the development of nurturing techniques such as environmental stimuli and the benefits of touch. The detrimental implications of lack of opportunity to experience a causal effect relationship at this stage of development has recently been recognized. However, little research exists at this time on structured learning opportunities while the infant remains in the medical environment. The benefits compared to the limitations of early intervention programs have yet to be demonstrated, and in accordance with the invention there is provided a system and method which provides for early intervention which may offset long-term neurological impairment.

The infant sucking response is a behavior that is critical for both survival and neurological development. The fetal sucking reflex typically develops in the 34th week of gestation. Thus, in the case of the infants in the study conducted in accordance with the invention, the fetal sucking reflex had not yet developed. Extended time spent in a non-nutritive sucking has been observed to be a primary behavior of the 3rd trimester fetus. More specifically, sucking is the first rhythmic behavior in which the infant engages and may contribute to neurological development by establishing internally regulated rhythms. Since in neonatal intensive care, medical and environmental constraints inhibit non-nutritive sucking opportunity, and very premature infants born as early as 24 weeks gestation have only a 56% probability of surviving, but demonstrate impaired neurological development, these critically premature infants often need physical therapy to develop sustained feeding capability, and a sucking response strong enough to allow them to gain adequate daily nutrition by mouth. Prior research on non-nutritive sucking has shown that it can increase daily weight gain when paired with tube feedings of the infant.

It has been demonstrated that auditory capability is one of the earliest discriminitive abilities of the fetus. At 18 weeks gestation age, increased heart rate to loud sounds has been noted, and at 25–27 weeks the majority of fetuses begin to give inconsistent responses to sound. At 29 weeks, the developing fetus consistently responds to auditory stimuli. At 30–35 weeks, the fetus is hearing maternal sounds, responding to these sounds and beginning to discriminate among speech sounds, particularly with regard to pitch and rhythm. At 40 weeks, the full term infant can recognize its mother's voice, prefers women's voices, can recognize stories and melodies heard during the final trimester of development, and prefers his or her native language.

In accordance with the method of the invention, the contingent effects of music on premature infant behavior, specifically to determine whether the pacifier activated lullaby music would reinforce non-nutritive sucking rates of premature infants who were evaluated as poor feeders by the neonatal intensive care unit, was conducted.

Examples

A study was conducted in which the participants were twelve premature infants (six male and six female) born at an average gestation age of 29.3 weeks and an average weight of 2 lbs. 4.8 oz. The average adjusted gestation age at the time of the test study was 35.5 weeks with weight averaging 3 lbs. 8.6 oz. Individual infant demographics are shown in Table 1 as follows.

TABLE 1

Participant Demographics

| Gender | Gestational Age (GA) Birth | Birthweight | Adjusted GA at Study | Weight at Study |
|---|---|---|---|---|
| F | 30 wks | 2 lbs. 11 oz. | 33.0 wks | 3 lbs. 5.2 oz. |
| F | 28 wks | 2 lbs. 0 oz. | 34.2 wks | 3 lbs. 13.4 oz. |
| F | 33 wks | 3 lbs. 9 0z. | 34.3 wks | 3 lbs. 14.8 oz. |
| F | 31 wks | 3 lbs. 1 oz. | 35.0 wks | 4 lbs. 0.8 oz. |
| F | 31 wks | 2 lbs. 12 oz. | 35.0 wks | 3 lbs. 8.6 oz. |
| F | 24 wks | 1 lb. 12 oz. | 32.0 wks | 3 lbs. 4.4 oz. |
| Female Mean | 29.5 wks | 2 lbs. 10.2 oz | 33.9 wks | 3 lbs. 10.5 oz. |
| M | 31 wks | 2 lbs. 5.7 oz. | 40.2 wks | 4 lbs 1.0 oz. |
| M | 27 wks | 1 lb. 7.9 oz. | 41.0 wks | 4 lbs 1.0 oz. |
| M | 32 wks | 2 lbs. 12.4 oz. | 34.5 wks | 4 lbs. 4.0 oz. |
| M | 29 wks | 1 lb. 15.0 oz. | 40.0 wks | 4 lbs. 4.2 oz. |
| M | 32 wks | 3 lbs. 0 oz. | 34.3 wks | 3 lbs. 12.8 oz. |
| M | 24 wks | 2 lbs 0.7 oz. | 33.0 wks | 4 lbs. 1.0 oz. |
| Male Mean | 29.2 wks | 2 lbs. 4.2 oz. | 37.2 wks | 4 lbs. .8 oz. |

It may be noted that male infants were equivalent in gestational age at birth to females, but were lower in birth weight. This is a typical gender difference of premature infants since male fetal development is approximately two weeks behind that of females. At the time of conducting the test study the male infants were older than the female infants, demonstrating a typical gender difference of male failure to thrive as compared to females.

The infants were referred for participation by a specialist trained in premature infant development and criteria for participation were that the infant must be a poor feeder, must have achieved approximately 34 weeks adjusted gestational age, and must be able to tolerate two simultaneous types of stimulation (pacifier and auditory stimulation).

Participation for specific infants was discontinued based on infant distress which included irregular respiration or apnea, flushing or mottling of skin, tremors, startles, flayed fingers or hand in stop position, facial twitches, eye rolling or floating, whimpering, hiccoughing, spitting up, gagging or grunting.

Methodology of the Test

The infants participated in this study while in the isolette or crib. They were deliberately not held to avoid adding a third type of stimulation. At this gestation age sensory stimulation is cumulative and easily overwhelms the infant. The specially adapted pacifier was offered between 4–5 PM in the interval of one hour past the last feeding and at least one hour prior to the next feeding. The study was conducted across fourteen minutes with a silence condition for the first two minutes of baseline, then five minutes of contingent music, followed by another two minute period of silence and another five minutes of contingent music. The study was designed to stay within the fifteen minute maximum length of stimulating interaction allowed with the infant at this stage of development.

The pacifier 13 which was used is one known as the Minimam Newborn Orthodontic Pacifier by Ross Laboratories, part #50486, and was adapted so that a suck of predetermined strength activated the cassette recorder 35 for a specified length of time through a pressure transducer 19 as shown in FIG. 1. Pressure sensitivity and length of music activation could be controlled for each suck and for the purpose of this study were set at 15% pressure to activate ten seconds of music. The music played was a selection of commercially recorded lullabies sung by female vocalists played free field at 65–70 dB. Each suck strong enough to activate the music also activated an on/off red light on the control box 23, designating frequency while a second red light designating duration was simultaneously activated for ten seconds following each suck. Data were recorded across the fourteen minutes for each five second interval in which the duration light was activated for at least three seconds.

Results

Figure 3:
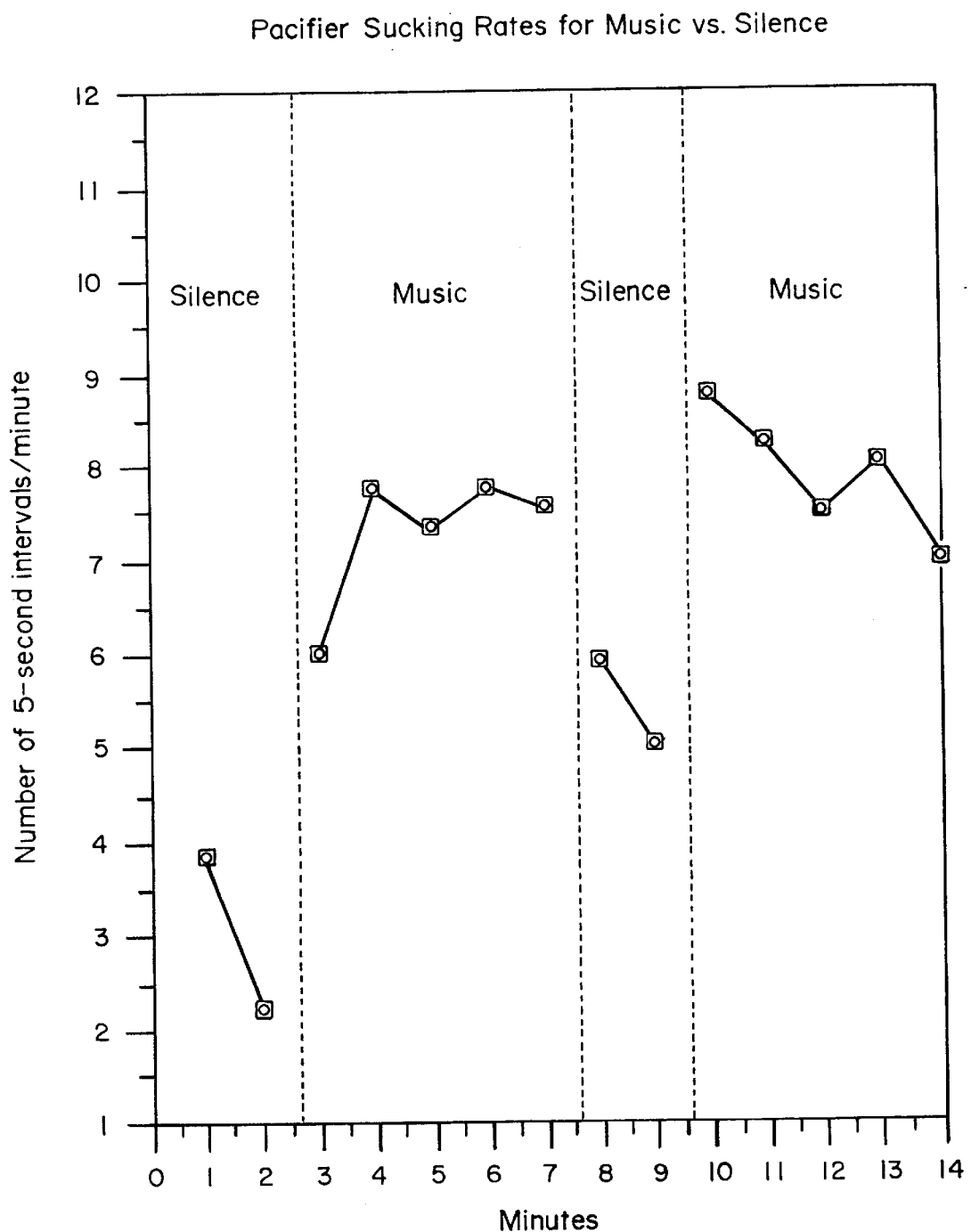
FIG. 3 a graph showing typical pacifier sucking rates for music as compared to pacifier sucking rates for silence from a sampling of premature infants.

The results for all infants are shown in FIG. 3 and demonstrate that sucking rates consistently increased across time during the first contingent music interval then dropped substantially during the second baseline condition. Sucking rates were the highest in the first minute of the second contingent music condition. Overall, sucking rates during music were 2.43 times as great as those during silence. Infants averaged a sucking rate of 15 seconds/minute during silence increasing to 37.7 seconds/minute during music. The data indicate infant learning and discrimination of music on/off conditions and show music to be an effective reinforcer for non-nutritive sucking for this limited time period. The music condition shows a steady decline in sucking rate across the five minute interval which may be attributable to fatigue or to the infant lulling him/herself to sleep prior to the end of the trial.

Figure 4:
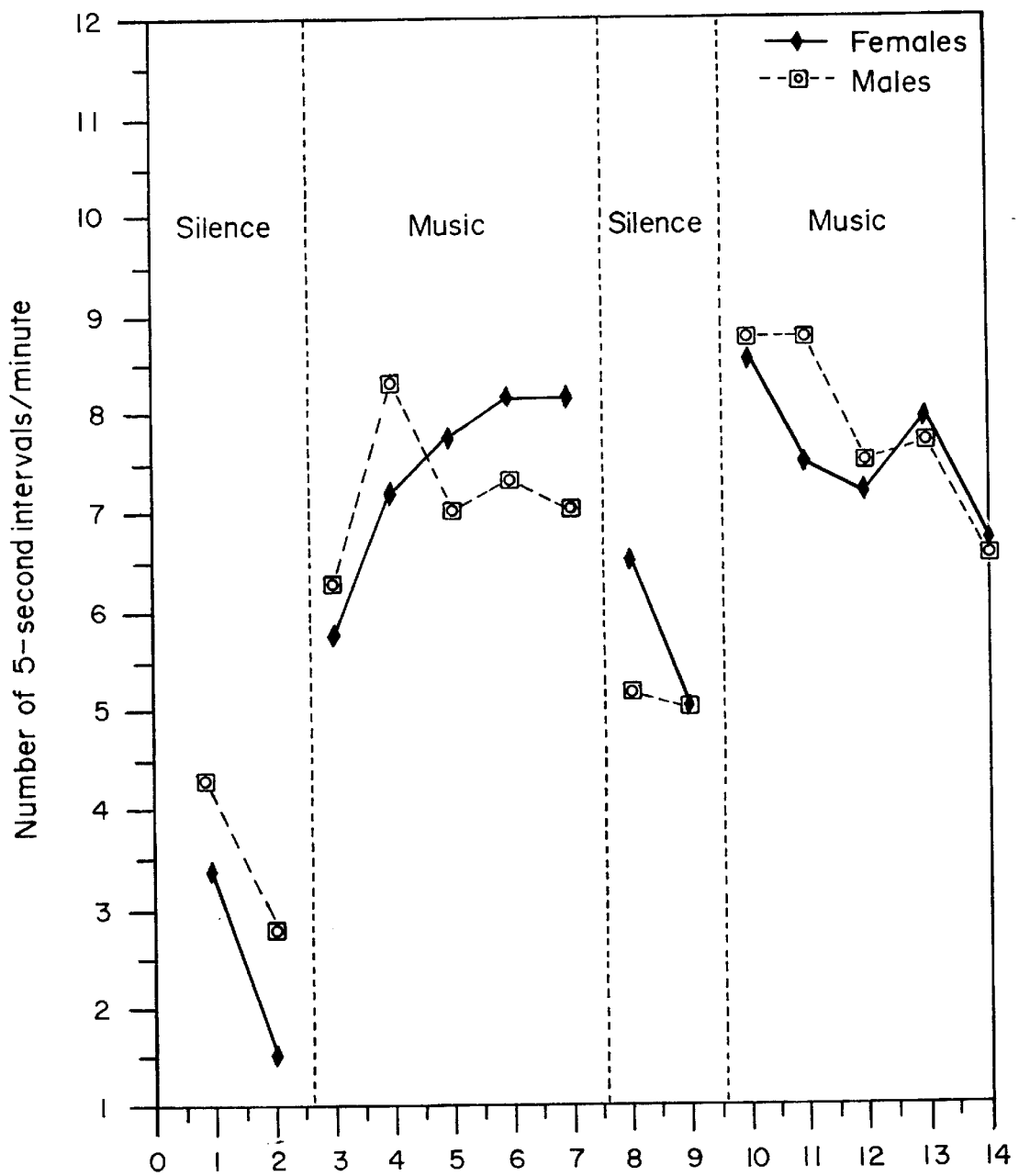
FIG. 4 is a graph similar to that of FIG. 3, but showing typical pacifier sucking rates for both music and silence by gender, i.e., distinguishing males from females.

Analysis of the data by gender is shown in FIG. 4 and demonstrates that males sucked the pacifier at a slightly greater rate under all conditions than did females. Females however, were much steadier and consistent in their learning responses. During the study, it was noted that four of the six female participants continued to suck strongly for several minutes past the fourteen minute time limit for data collection, while four of the six male participants ceased to suck and appeared asleep by minutes 13–14 of data collection. The gender differences are viewed with caution however, due to the small number of subjects in each group.

Despite the fragility of the participants, all showed increased sucking responses to music. The infants adapted to the music cutting on and off and showed no startle responses to the events. None of the subjects exhibited signs of over-stimulation during the experimental trials and no evidence of over-stimulation was reported by the nursing staff. Sucking seemed to be highly pleasurable when subjectively observed, and sustained, with many infants continuing to suck for several minutes past the data collection period and several sucking themselves to sleep. The intervention increased non-nutritive sucking rates with no negative side effects noted.

The results of the test showed that the very young infants are capable of learning and the graphs reflect learning curves that are clear and defined. The graphs shown in FIGS. 3 and 4 demonstrate that the pre-term babies discriminated on/off music conditions and that there appeared to be slight gender differences in learning styles. The music pacifier system 11 functioned to reinforce infants' non-nutritive sucking which has implications for their neurological development and feeding skill or duration.

Having thus described the invention, the same is set forth in a non-limiting manner in the appended claims.

What is claimed is:

1. A pacifier system, comprising a pacifier for being sucked on;
   sensing means for sensing duration and intensity of sucking on the pacifier
   auditory stimulus means for providing auditory stimulus in response to said sucking on said pacifier; and
   means for activating said auditory stimulus means to provide said auditory stimulus for a predetermined amount of time upon said sensing means sensing sucking on said pacifier for a predetermined minimum amount of time and sensing sucking of a minimum intensity.

2. A pacifier system as in claim 1 wherein said auditory stimulus means comprises a source of played music.

3. A pacifier system as in claim 1 wherein said auditory stimulus means comprises a source of spoken language.

4. A pacifier system as in claim 1 wherein said sensing means is adapted for detecting a specified suck profile for having said means for activating said auditory stimulus means upon said sensing means sensing sucking on said pacifier for a predetermined minimum amount of time, of a minimum intensity and of the specified suck profile.

5. A pacifier system as in claim 4 wherein said sensing means is adapted to detect minimum intensity of sucking, minimum duration of sucking, maximum duration of sucking, minimum frequency and maximum frequency to determine the suck type profile.

6. A pacifier system as in claim 5 further comprising recording means for continuously recording the suck profile by a frequency modulated recording of the analog suction waveform to provide an immediate indication of oral activity.

7. A pacifier system as in claim 1 wherein said auditory stimulus means comprises a tape player, said sensing means comprises a pressure transducer connected by said pacifier through an air tube to detect pressure changes in the pacifier, and said activating means comprises a control box to which said pressure transducer is connected, and to which said tape player is connected, and said control box having a sensitivity control for adjusting the sensitivity of such intensity detected to match a predetermined value before actuating the tape player, and a delay control for setting the amount of time of sucking at a predetermined intensity before actuating the tape player.

8. A pacifier system as in claim 7 further comprising at least one speaker for broadcasting the auditory stimulus.

9. A pacifier system as in claim 1 wherein said means for activating said auditory stimulus means comprises a programmed computer, said sensing means comprises a pressure transducer connected to said programmed computer and to said pacifier, and said auditory stimulus means comprises a tape player connected for activation by said programmed computer.

10. A pacifier system as in claim 9 wherein said programmed computer further comprises a display for displaying a recorded suck profile of the analog suction waveform of a human sucking on the pacifier.

11. A method of modifying a sucking response, comprising detecting the intensity of sucking and duration of sucking on a pacifier; and upon detection of a predetermined intensity of sucking for a predetermined amount of time, providing an auditory stimulus.

12. A method as in claim 11 wherein said detecting comprises detecting the sucking of a premature infant on a pacifier.

13. A method as in claim 11 further comprising detecting the sucking profile of the sucking, and only providing said auditory stimulus upon said sucking matching a predetermined sucking profile.

14. A method as in claim 13 wherein said predetermined sucking profile is determined by detecting the values of a minimum intensity of sucking, a minimum duration of sucking, maximum duration of sucking, a minimum frequency of sucking and a maximum frequency of sucking, whereby only sucking profiles falling within said values are used to provide said auditory stimulus.

15. A method as in claim 11 wherein said auditory stimulus provided is music to premature infants sucking on a pacifier to reinforce non-nutritive sucking response.

16. A method as in claim 11 wherein said auditory stimulus provided is spoken language to infants to teach language.

17. A method as in claim 11 further comprising storing and displaying the detected suck profile to provide a real time indication of oral activity.

18. A method as in claim 11 wherein said auditory stimulus is provided for a predetermined period of time.

19. A method as in claim 11 wherein said auditory stimulus is provided only for so long as sucking with said predetermined sucking profile occurs.

20. A method as in claim 11 wherein said predetermined intensity of sucking must be detected for a predetermined minimum period of time before said auditory stimulus is provided.

* * * * *